US00PP09333P

United States Patent [19]

Zaiger et al.

[11] Patent Number: Plant 9,333

[45] Date of Patent: Oct. 17, 1995

[54] NECTARINE TREE "HONEY KIST"

[76] Inventors: Chris F. Zaiger, 929 Grimes Ave.; Leith M. Gardner, 1207 Grimes Ave.; Gary N. Zaiger, 1907 Elm Ave.; Grant G. Zaiger, 4005 California Ave., all of Modesto, Calif. 95358

[21] Appl. No.: 362,231

[22] Filed: Dec. 22, 1994

[51] Int. Cl.[6] ..... A01H 5/00

[52] U.S. Cl. ..... Plt./41.1

[58] Field of Search ..... Plt./41.1

*Primary Examiner*—James R. Feyrer

[57] ABSTRACT

The new and distinct nectarine tree has the following unique combination of features that are outstanding in a new variety:

1. Fruit with excellent flavor and eating quality.
2. Fruit with firm yellow flesh, good storage and shipping quality.
3. Fruit that will stay firm on the tree two weeks after maturity (shipping ripe).
4. Fruit with an attractive red skin color.
5. Heavy and regular production of fruit.
6. Vigorous upright growth.

1 Drawing Sheet

ORIGIN OF THE VARIETY

Our new and distinct variety of nectarine tree was originated by us in our experimental orchard located near Modesto, Calif., as a first generation cross between two selected seedlings with the field identification numbers 36ER86 and 9GC175. The maternal parent 36EB86 originated from a second generation seedling that was selected from a cross between May Grand Nectarine (U.S. Plant Pat. No. 2,794) and a peach of unknown parentage. The pollen parent 9GC175 originated from a second generation seedling of a cross between an open pollinated seedling of Early Sun Grand Nectarine (U.S. Plant Pat. No. 1,420) and Royal Gold Peach (U.S. Plant Pat. No. 2,663). A large group of seedlings from this first generation cross were planted and grown under careful observation by us; one such seedling, which is the present variety, having especially desirable fruit characteristics was selected for asexual reproduction and commercialization.

ASEXUAL REPRODUCTION OF THE VARIETY

The present new variety of nectarine tree was asexually reproduced by budding, as performed by us, in our experimental orchard located near Modesto, Calif., which shows that all characteristics of the tree and its fruit run true to the original form and are established and transmitted in succeeding propagations.

SUMMARY OF THE VARIETY

The new and distinct variety of nectarine tree is of large size, vigorous, upright growth and is a regular and productive bearer of large size, yellow flesh, clingstone fruit with excellent flavor and eating quality. The fruit is further characterized by having firm flesh, the ability to be shipped to long distance markets, being relatively uniform in size throughout the tree, and in comparison to Early Sun Grand Nectarine (U.S. Plant Pat. No. 1,420) the new variety has the ability to produce more uniform size fruit, to produce fruit without split pits, to produce fruit that holds firm on the tree longer after maturity with a sweeter, more mild subacid flavor and is approximately 2 weeks later in maturity.

BRIEF DESCRIPTION OF THE PHOTOGRAPHS

Typical specimens are shown in the accompanying color photographs of the foliage and fruit of the new nectarine variety. The upper and lower surface of the leaves are illustrated with an exterior view of the fruit and a fruit divided in the suture plane to reveal flesh coloration and a stone remaining in place. The photographs were taken shortly after the fruit was picked at maturity (firm ripe) and the colors are as nearly true as is reasonably possible in a color representation of this type.

DESCRIPTION OF THE VARIETY

The botanical details of the new and distinct variety of nectarine tree, its fruit, flowers and foliage are based upon observations of specimens grown near Modesto, Calif., with color terminology (except those in common terms) in accordance with Reinhold Color Atlas by A. Kornerup and J. H. Wanscher.

Tree:

*Size.*—Large.
*Vigor.*—Vigorous.
*Form.*—Upright.
*Density.*—Medium dense.
*Production.*—Productive.
*Bearer.*—Regular.

*Trunk:*

*Size.*—Large.
*Texture.*—Medium shaggy.
*Color.*—Brown to tobacco brown (5-F-4) to (5-F-6).

Branches:

*Size.*—Medium.
*Texture.*—Smooth to medium rough.
*Lenticels.*—Numerous. Large Size.
*Color.*—Light brown to dull brown.

Leaves:

*Size.*—Large. Average length — 6½". Average width — 1½".
*Form.*—Lanceolate. Pointed.
*Texture.*—Smooth.
*Thickness.*—Medium.
*Margin.*—Crenate.
*Petiole.*—Medium length. Medium thickness.
*Glands.*—Reniform. Number varies from 1 to 4. Average number 2. Located on upper portion of petiole and lower portion of leaf blade.

*Color.*—Upper surface — green to dark green (27-F-5) to (27F-7). Lower surface — graylish green to dull green. (28-E-6) to (28E-7).

Flower buds:

*Size.*—Medium to large.

*Form.*—Plump.

*Pubescence.*—Pubescent.

Flowers:

*Size.*—Large — showy.

*Blooming period.*—Mar. 14, 1993 to Mar. 10, 1993. Varies slightly with climatic conditions.

*Pollen.*—Present. Self fertile.

*Color.*—Pink.

Fruit:

*Maturity when described.*—Firm ripe.

*Date of first picking.*—Jun. 17, 1993.

*Date of last picking.*—Jun. 22, 1993.

*Size.*—Large. Average diameter axially 2¾". Average transversely in suture plan — 2¾".

*Form.*—Nearly globose.

*Suture.*—Shallow — extends from base to apex.

*Ventral surface.*—Varies from nearly rounded to slightly lipped.

*Cavity.*—Rounded to slightly elongated in suture plane. Average depth — ½". Average breadth — ¾".

*Base.*—Retuse.

*Apex.*—Rounded to slight retuse.

Flesh:

*Ripens.*—Evenly.

*Texture.*—Firm — meaty.

*Juice.*—Moderate.

*Fibers.*—Few — tender.

*Aroma.*—Moderate.

*Amygdalin.*—Undetected.

*Flavor.*—Excellent, mild sweet, subacid.

*Eating quality.*—Excellent.

*Color.*—Varies from yellow to maize yellow (4-A-5) to (4-A-6). Pit cavity varies from yellow to grayish yellow (4-E-6) to (4-D-6).

Skin:

*Thickness.*—Medium.

*Texture.*—Medium — tenacious to flesh.

*Tendency to crack.*—None.

*Down.*—Wanting.

*Color.*—Light yellow to yellow ground color (2-A-5) to (2-A-6). Overspread with turkish red to cardinal red (10-C-8) to (10-D-8).

Stone:

*Type.*—Clingstone.

*Size.*—Medium to large. Average length 1½". Average width 1⅛". Average thickness ¾".

*Form.*—Ovoid.

*Base.*—Usually rounded, varies from straight to rounded.

*Apex.*—Cuspidate — small to medium size.

*Sides.*—Mostly unequal — varies from equal to unequal.

*Surface.*—Irregularly furrowed toward apex, pitted toward base. its elongated to round in shape.

*Ridges.*—Rounded.

*Tendency to split.*—None.

*Color.*—Brown to reddish brown (8-C-7) to (8-D-7).

Use: Dessert.

*Market.*—Local and long distance.

Keeping quality: Good.

Shipping quality: Good.

The nectarine tree, its flowers, foliage and fruit herein described may vary in slight detail due to climatic, soil conditions and cultural practices under which the variety maybe grown. The present description is that of the variety grown under the ecological conditions prevailing near Modesto, Calif.

We claim:

1. A new and distinct variety of nectarine tree, substantially as illustrated and described, characterized by its large size, vigorous upright growth, and which is a productive and regular bearer of large size, yellow flesh, clingstone fruit with excellent flavor and eating quality. The fruit is further characterized by holding firm on the tree two weeks after maturity (shipping ripe), having the ability to be shipped to long distance markets and in comparision to Early Sun Grand Nectarine (U.S. Plant Pat. No. 1,420) the new variety has the ability to produce more uniform size fruit which matures approximately 2 weeks later.

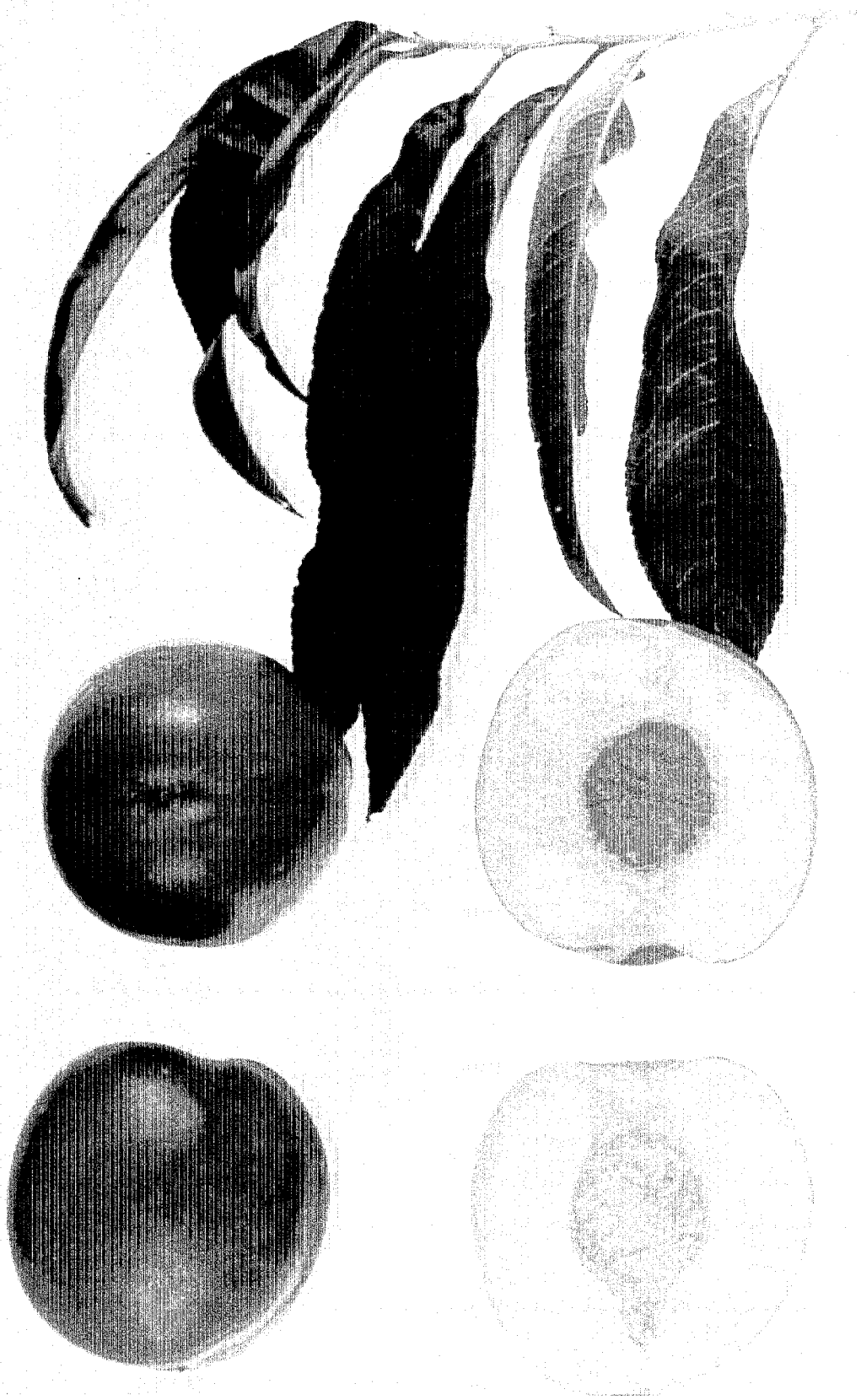

* * * * *